(12) United States Patent
Lee et al.

(10) Patent No.: US 8,663,451 B2
(45) Date of Patent: Mar. 4, 2014

(54) LINKER, IMPEDANCE BIOCHIP, AND METHOD OF QUANTITATIVELY DETECTING TARGET ANALYTE IN FLUID SAMPLE USING THE BIOCHIP

(75) Inventors: Chih-Kung Lee, Taipei (TW); Adam Shih-Yuan Lee, Taipei (TW); Ching-Sung Chen, Taipei (TW); Ku-Ning Chang, Taipei (TW); Ying-Hua Chen, Taipei (TW); Bryan Yong-Jay Lee, Taipei (TW)

(73) Assignee: National Taiwan University, Taipei (TW)

( * ) Notice: Subject to any disclaimer, the term of this patent is extended or adjusted under 35 U.S.C. 154(b) by 251 days.

(21) Appl. No.: 13/161,702

(22) Filed: Jun. 16, 2011

(65) Prior Publication Data

US 2012/0067742 A1  Mar. 22, 2012

Related U.S. Application Data

(60) Provisional application No. 61/383,930, filed on Sep. 17, 2010.

(51) Int. Cl.
*G01N 27/327* (2006.01)
(52) U.S. Cl.
USPC ............... 205/777.5; 205/792; 204/403.1; 204/403.04; 204/40.14; 549/59

(58) Field of Classification Search
USPC ............... 205/782, 792; 204/403.01, 403.14; 549/59
See application file for complete search history.

(56) References Cited

U.S. PATENT DOCUMENTS 7,129,363 B2 * 10/2006 Han et al. .................. 549/71
2012/0329037 A1 * 12/2012 Zhang et al. ................. 435/5

OTHER PUBLICATIONS

Daniels et al. (Electroanalysis 19, 2007, No. 12, 1239-1257).*

* cited by examiner

*Primary Examiner* — Luan Van
*Assistant Examiner* — Steven Rosenwald
(74) *Attorney, Agent, or Firm* — Edwards Wildman Palmer LLP; Peter F. Corless; Richard B. Emmons

(57) ABSTRACT

The present invention provides a linker for joining an electrode and a capture probe on a biochip, and a biochip comprising the linker. The impedance baseline of the linker of the present invention is three orders lower than the conventional long chain thiol linker when adopting in a fadaraic impedance biochip construction. With lower impedance baseline, the device designed to measure the signal of the biochip of the present invention could be further simplied on the electrical circuit design and be made in lower cost, compacter size and get the potential to be used in point-of-care applications. The present invention also provides a method of quantitatively detecting a concentration of a target analyte in a fluid sample by adopting the biochip and the linker of present invention.

15 Claims, 5 Drawing Sheets

(A)

(B)

LINKER, IMPEDANCE BIOCHIP, AND METHOD OF QUANTITATIVELY DETECTING TARGET ANALYTE IN FLUID SAMPLE USING THE BIOCHIP

CROSS-REFERENCE TO RELATED APPLICATIONS

This application claims the benefit of U.S. Provisional Application No. 61/383,930, filed on Sep. 17, 2010, the entire contents of which is incorporated herein by reference.

BACKGROUND OF THE INVENTION

1. Field of the Invention

The present invention relates to linkers on biochips, and more particularly, to a linker of bridging an electrode and a capture probe on a biochip.

2. Description of Related Art

A biochip is a chip designed to detect or quantify a target analyte such as protein, DNA, cell, glucose, cardiomyopathic biomarkers (e.g., S100 and C-Reactive protein (CRP), Troponin I, CKMB and the like), cancer biomarkers (e.g., cancer antigen 125 (CA125), carcinoembryonic antigen (CEA), prostate-specific antigen (PSA) and the like), bacterium biomarkers (e.g., *E. Coli, staphylococcus* and the like), and virus (e.g., H1N1 and the like. Many biochips are affinity-based that use an immobilized capture probe to bind the target analyte and then use a transducer to detect a change at a localized surface. The capture probe is a bio-recognition element that could bind or interact with the target analyte. For example, the capture probe may be an antibody when the target analyte is an antigen. The change could be measured in a variety of ways. Among these selections, an impedance biochip that measures the electrical impedance of an interface between an electrode and a fluid sample has the advantages of label free, low cost, low power consumption and ease of miniaturization. Due to these benefits, the impedance biochip is more suitable for application where small size and cost issues are crucial, such as point-of-care diagnostics.

The impedance biochip can be divided into two groups: non-faradaic and faradaic. A non-faradaic biochip, also called a capacitance biochip, detects the concentration of target analyte (e.g., biomarker) by measuring the non-faradaic transient current or capacitance change of the electrode-solution interface. Capacitance difference corresponding to various analytes comes from the changes in the dielectric constant, charge distribution, dimension and shape when the biomarker-capture probe interaction occurs on the electrode-solution interface. The capacitance biochip has a drawback that forming a defect-free bio-recognition layer is more crucial than that in the faradaic biochip, because if the defect-free boo-recognition layer is not well insulated, ions can move through a defect area, and cause short circuiting leading to a decrease or absence of the signal.

In contrast, the faradaic biochip measures the faradaic current changes caused by the oxidation/reduction (redox) reaction of redox-active species. Thus, faradaic biochip requires the addition of a redox-active species. Steric hindrance resulted from binding between the immobilized capture probe and the target analyte will form a barrier to stop the diffusion of redox-active species from the solution to the electrode, therefore, fewer faradaic current will be detected when there are more target analyte in the fluid sample. By further calculating a current-voltage ration that gives the impedance, one can easily correlate the concentration of the target analyte with the calculated impedance.

A linker is the special molecular utilized to immobilize the capture probe on a biochip. It is critical that the capture probe be attached to the biochip surface in a way that maintains probe specificity and activity while inhibiting nonspecific binding. The most common types of linkers are based on thiols bound to gold surfaces and silanes to oxide surfaces. For biochips that adopt surface plasmon resonance or quartz crystal microbalance to measure the target analyte correlated change, a tightly-packed self-assembled monolayers (SAMs) is preferred in order to block access of most solution species to the electrode in the biochip. Linker with long chain thiol, such as an alkanethiol like 12-mercaptododecanoic acid (HS$(CH_2)_{11}$COOH, "12-MCA"), is more desirable. However, in the case of faradic impedance biochip where the electrode surface of the impedance biochip needs to be accessible to the redox species, these conventional adopted linkers are not suitable anymore.

In this regard, there is still a need from the industries to develop a linker for joining the capture probe to an electrode of the impedance biochip, which has higher conductivity and lower block effect for the redox-active species.

SUMMARY OF THE INVENTION

In view of the problems of the prior art, an embodiment of the present invention provides a linker for joining a capture probe to an electrode in a biochip, comprising a compound of formula (I): $R^2$—$(CH_2)_m$—$(R^3)_n$—$(CH_2)_k$—$R^1$ (I), wherein R' is a functional group for binding the capture probe such as protein, DNA, RNA, or enzyme; $R^2$ is a functional group for connecting the electrode such as Au, Pt, Ag, and ITO; $R^3$ is a thiophene or thiophene derivative; n is 1 to 4; m is 0 to 5; and k is 0 to 5.

In another embodiment of the present invention, a linker for joining a capture probe to an electrode in a biochip comprises a compound of formula (I): $R^2$—$(CH_2)_m$—$(R^3)_n$—$(CH_2)_k$—$R^1$ (I), wherein R' is a hydrogen atom, a chain aliphatic hydrocarbon group optionally having substituent(s), —C(=O)—$R^{11}$, —C(=O)—O—$R^{11}$, $NH_2$, or epoxide; $R^2$ is —SH, S—C(=O)—$R^{11}$, sulfide, disulfide or silane; $R^3$ is a 5- to 7-membered sulfur-containing aromatic heterocyclic group optionally having substituent(s); $R^{11}$ is a hydrogen atom, or $C_{1-6}$ alkyl optionally having substituent(s); n is 1 to 4; m is 0 to 5; and k is 0 to 5.

An embodiment of the present invention further provides an biochip for quantitatively detecting a concentration of a target analyte in a fluid sample, comprising: at least two electrodes; a linker having compound of formula (I) and a capture probe for interacting with the target analyte in the fluid sample, wherein the linker has two terminals individually connect if the capture probe and the electrode, thereby joining the capture probe to the electrode.

Another embodiment of the present invention further provides a method of quantitatively detecting a concentration of a target analyte in a fluid sample, comprising: providing the target analyte in the fluid sample on the above-mentioned biochip; providing a redox specie into the fluid sample; applying a potential profile with an alternative current (AC) frequency onto the electrode of the biochip during a period of time and measuring the current response needed to maintain the potential profile simultaneously, wherein the potential profile consists of a direct current (DC) bias and any alternative current (AC) wave; and associating a current signal generated from the biochip with a concentration of the target analyte in the fluid sample.

According to the embodiment of the present invention, the biochip which adopts the linker comprising a compound of formula (I), provides a more electrically accessible surface to the redox species, so as to increase the faradaic current induced by the redox species. The advantage of increasing faradaic current is that the electronic circuit for measuring the impedance of the biochip surface can be designed more compact and at lower cost, and thus is more suitable for point-of-care applications.

BRIEF DESCRIPTION OF THE DRAWINGS

The above and other aspects, features and other advantages of the present invention will be more clearly understood from the following detailed description taken in conjunction with the accompanying drawings, in which.

In the drawings, the shapes and dimensions may be exaggerated for clarity, and the same reference numerals will be used throughout to designate the same or like components.

DETAILED DESCRIPTION OF THE PREFERRED EMBODIMENTS

The detailed description of the present invention is illustrated by the following specific embodiments. The invention may, however, be embodied in many different forms and should not be construed as being limited to the embodiments set forth herein. Rather, these embodiments are provided so that this disclosure will be thorough and complete, and will fully convey the scope of the invention to those ordinarily skilled in the art. Persons ordinarily skilled in the art can conceive the other advantages and effects of the present invention based on the disclosure contained in the present specification.

Figure 1:
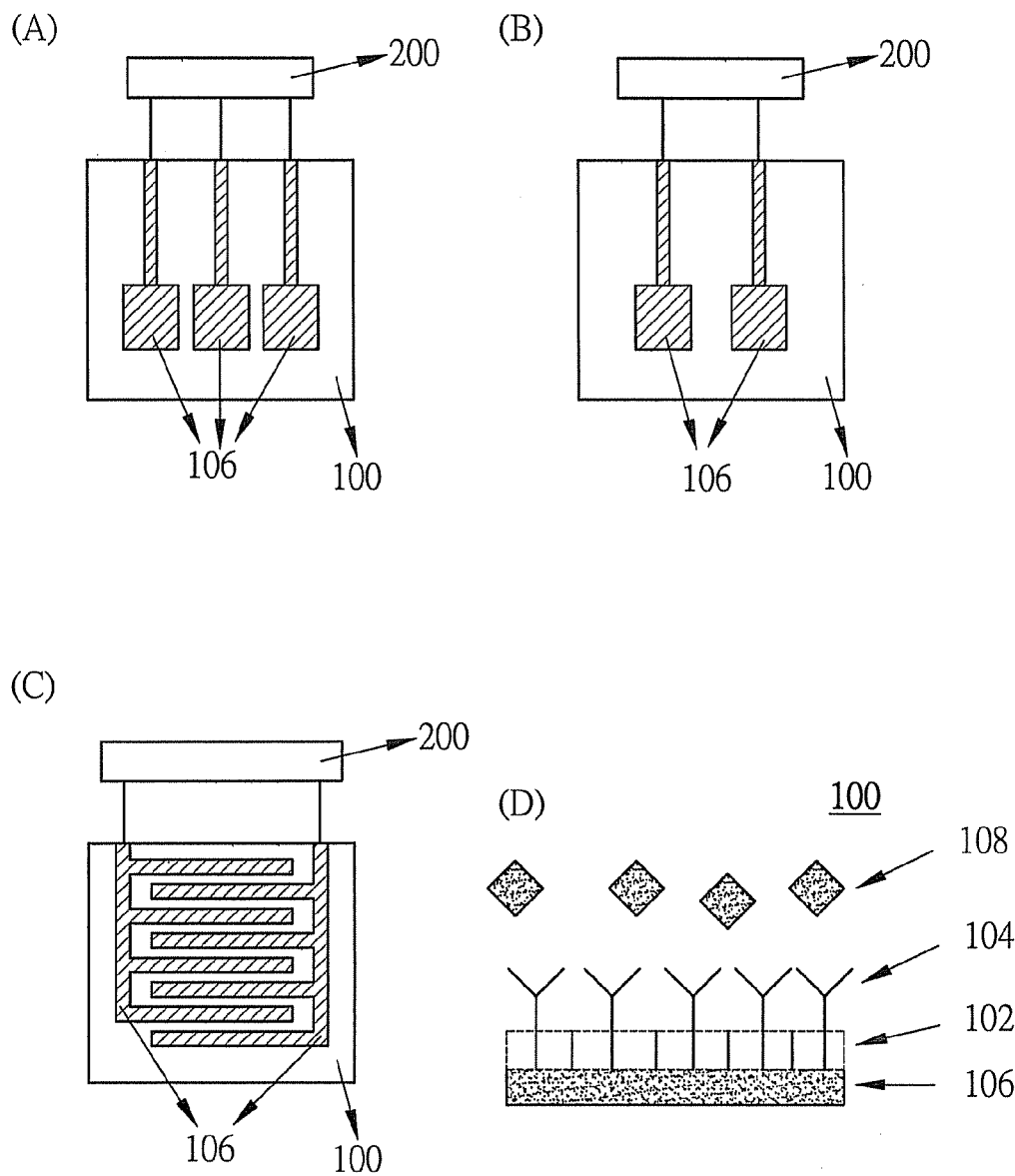
FIG. 1(A) is a schematic diagram for measuring the impedance of a biochip comprising: a biochip 100 having three electrodes 106 according to an embodiment of the present invention; and an electrochemical analyzer 200 for providing a potential profile and measuring a current response needed to maintain the potential profile.
FIG. 1(B) is a schematic diagram for measuring the impedance of a biochip 100 having two electrodes 106 according to another embodiment of the present invention.
FIG. 1(C) is a schematic diagram for measuring the impedance of a biochip 100 having two electrodes 106 according to still another embodiment of the present invention.
FIG. 1(D) is a schematic diagram of an electrode 106 having linkers 102 and capture probes 104 thereon and target analytes 108 in the fluid sample.

FIG. 1(D) is a schematic diagram which shows a linker 102 for joining a capture probe 104 to an electrode 106 of the biochip 100 and a target analyte 108 in the fluid sample. As an embodiment of the present invention, a linker for joining a capture probe to an electrode of a biochip, comprising a compound of formula (I):

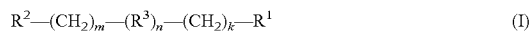
$$R^2-(CH_2)_m-(R^3)_n-(CH_2)_k-R^1 \qquad (I)$$

wherein $R^1$ is a functional group for binding the capture probe such as protein, DNA, RNA, or enzyme, preferably a —C(=O)—OH, —C(=O)H, —NH$_2$ or epoxide; $R^2$ is a functional group for connecting the electrode such as Au, Pt, Ag, and ITO, preferably a —SH, —S—C(=O)—CH$_3$, sulfide, disulfide or silane; $R^3$ is a thiophene or thiophene derivative; n is 1 to 4; m is 0 to 5; and k is 0 to 5. As an embodiment of the present invention, the linker comprises the formula (I) of $R^2-(CH_2)_m-(R^3)_n-(CH_2)_k-R^1$, wherein $R^1$ is —C(=O)—OH or —C(=O)H; $R^2$ is —SH or —S—C(=O)—CH$_3$; $R^3$ is a thiophene; n is 1 to 3; m is 0 to 3; and k is 0 to 3. Further, as an embodiment of the present invention, the linker comprising a compound selected from the group consisting:

5'-(mercapto)-[2,2'-bithiophene]-5-carbaldehyde,
5'-(mercapto)-[2,2'-bithiophene]-5-carboxylic acid,
5'-(mercaptomethyl)-[2,2'-bithiophene]-5-carbaldehyde,
5'-(mercaptomethyl)-[2,2'-bithiophene]-5-carboxylic acid,
5'-(2-mercaptoethyl)-[2,2'-bithiophene]-5-carbaldehyde,
5'-(2-mercaptoethyl)-[2,2'-bithiophene]-5-carboxylic acid,
5'-(3-mercaptopropyl)-[2,2'-bithiophene]-5-carbaldehyde, or
5'-(3-mercaptopropyl)-[2,2'-bithiophene]-5-carboxylic acid.

According to the embodiment of the present invention, the linker comprising a compound of formula (I) provide a more electrically accessible modified surface. When adopted in the faradaic impedance biochip which requires the addition of redox species to measure the surface impedance change induced by binding of target analyte and the capture probe, the linker of the present invention that offers a more electrically accessible surface can enhance the faradaic current. With lower impedance baseline, the device designed to measure the signal of the biochip of the present invention could be further simplied on the electrical circuit design and be made in lower cost, compacter size and get the potential to be used in point-of-care applications.

According to an embodiment of the present invention, the biochip 100 comprises at least two electrodes 106; a linker 102 which comprises a compound of formula (I); and a capture probe 104 for interacting with the target analyte 108 in the fluid sample, wherein the linker 102 has two terminals individually connect the capture probe 104 and at least one of the electrodes 106.

As an embodiment of the present invention, the biochip 100 has three electrodes and all the electrodes 106 are associated with the linkers 102 and the capture probes 104 as shown in FIG. 1(A). As an embodiment of the present invention, the biochip 100 has two electrodes and both the electrodes 106 are associated with the linkers 102 and the capture probes 104 as shown in FIG. 1(B). FIG. 1(C) illustrates the biochip 100 has two electrodes 106 of interdigital structure according to an embodiment of the present invention. As another embodiment, only a portion of the electrodes in biochip 100 are associated with the linkers 102 and the capture probes 104. Further, the biochip 100 can be connected to an electrochemical analyzer 200 as shown in FIGS. 1(A), (B)

and (C). As an embodiment of the present invention, the electrode is an electrical conductive material selected from the group consisting of Au, Pt, Ag, and ITO and the capture probe is at least one selected from the group consisting of protein, DNA, RNA, and enzyme. Further, as embodiment of the present invention, the linker having de-localized π electrons comprises a structure of thiophene, preferably
5'-(mercapto)-[2,2'-bithiophene]-5-carbaldehyde,
5'-(mercapto)-[2,2'-bithiophene]-5-carboxylic acid,
5'-(mercaptomethyl)-[2,2'-bithiophene]-5-carbaldehyde,
5'-(mercaptomethyl)-[2,2'-bithiophene]-5-carboxylic acid,
5'-(2-mercaptoethyl)-[2,2'-bithiophene]-5-carbaldehyde,
5'-(2-mercaptoethyl)-[2,2'-bithiophene]-5-carboxylic acid,
5'-(3-mercaptopropyl)-[2,2'-bithiophene]-5-carbaldehyde, or
5'-(3-mercaptopropyl)-[2,2'-bithiophene]-5-carboxylic acid.

As an embodiment of the present invention, a method of quantitatively detecting a concentration of a target analyte in a fluid sample, comprising: providing the target analyte in the fluid sample on a biochip having the linker that comprises a compound of formula (I) to immobilize the capture probe; providing redox specie (e.g., $Fe(CN)_6^{3-/4-}$, $Ru(NH_3)_6^{2+/3+}$, $Fe^{2+/3+}$, $Mn^{2+/3+}$, $Fe(NOTA)^{0/-}$, $[Fe(tacn)_2]^{3+/2+}$ and the likes) into the fluid sample; applying a potential profile with an alternative frequency onto the electrode of the biochip during a period of time and measuring the current response that needed to maintain the potential profile simultaneous, wherein the potential profile consists of a direct current (DC) bias, preferably ranging from −0.5 to 0.5 V, and an alternative current (AC) wave, preferably a sine wave, a triangle wave or a square wave, or a combination of a sine wave, a triangle wave and/or a square wave, in which the AC preferably has an amplitude ranging from 0.001 to 0.05 V; and associating a current signal generated from the impedance biochip with a concentration of the target analyte in the fluid sample. In the applied potential profile, the DC bias and AC amplitude may keep constant or vary during the period of time. The applied DC bias is set basically based on the selection of redox species (e.g., redox-active pairs) and the environment conditions, i.e. pH value.

As an embodiment of the present invention, the potential profile has a single AC frequency or switches between two or more AC frequencies during a period of time.

Impedance Measurements of Electrochemical Impedance Spectroscopy (EIS)

As an embodiment of the present invention, the electrochemical experiments were performed using a CHI 614D electrochemical analyzer (CH Instrument).

Cyclic voltammetry (CV) and impedance measurements were carried out in a three-electrode cell. In the three-electrode cell, the current no longer flow through reference electrode but through working and counter electrodes, thus the reference electrode can maintain the potential of a system.

Figure 2:
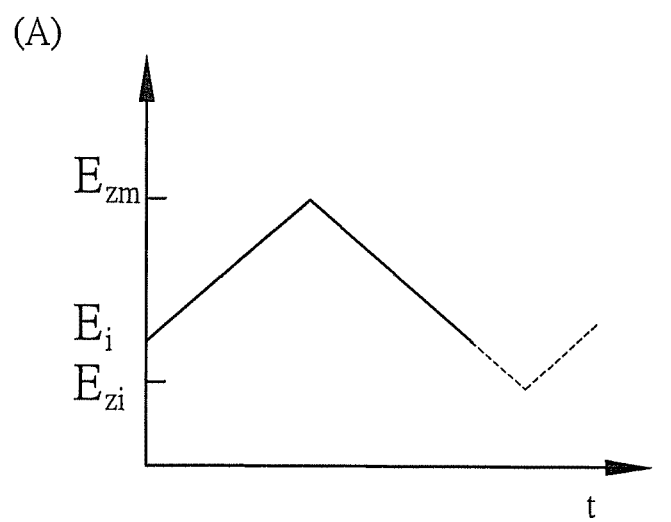
FIG. 2 shows CV diagram (A) applied potential profile vs. time; and (B) current response vs. applied potential profile.
Figure 2:
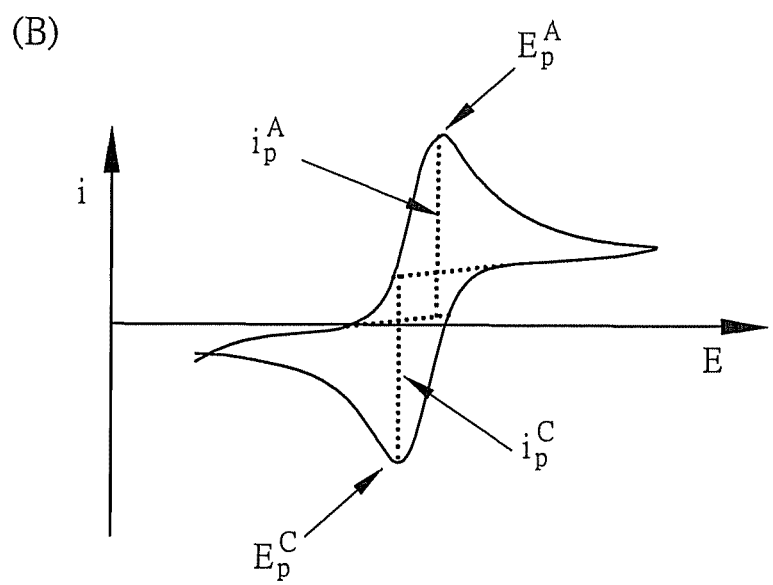
Figure 3:
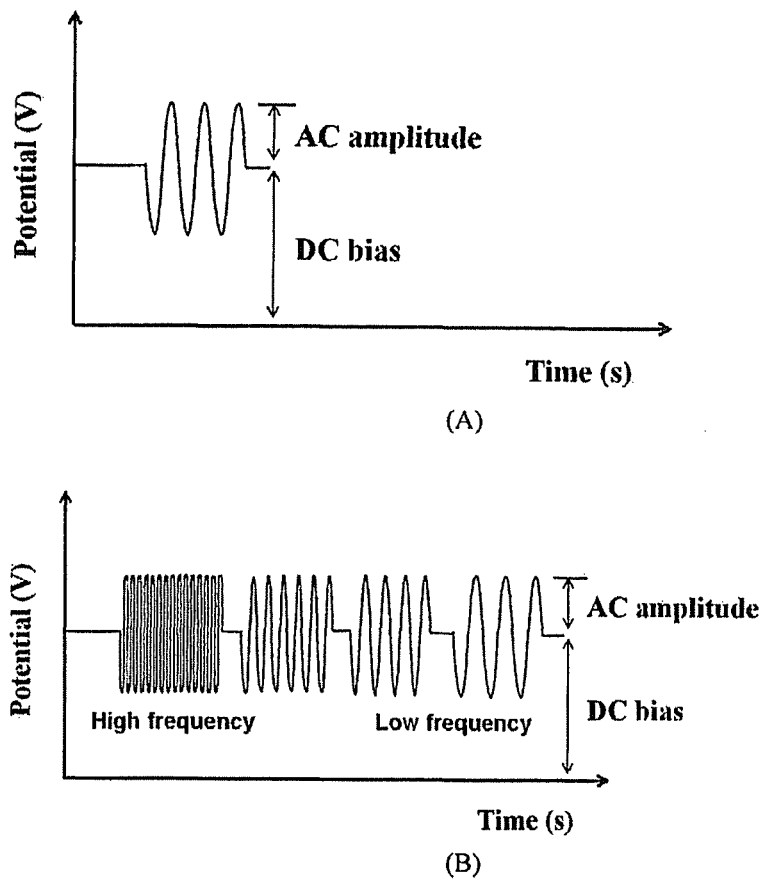
FIG. 3 shows, according to embodiments of the present invention, (A) a diagram of an applied potential profile includes two portions: a DC bias and an AC amplitude at a constant frequency, and (B) a diagram of an applied potential profile switched between two or more different frequencies.

FIG. 2 shows CV diagram (A) applied potential profile vs. time; and (B) current response vs. applied potential profile. The potential scan range for the CV was −0.2 to +0.6 V with a scan rate at 50 mV/s. For the impedance measurement, an applied potential profile includes two portions: a DC bias and an AC amplitude, as shown in FIG. 3(A). In an embodiment of the present invention, the DC bias voltage in the applied potential profile was set at the open-circuit potential of the redox pair with a 5 mV AC amplitude in a testing frequency range from 1 Hz to 100 kHz. FIG. 3(B) shows an embodiment that the frequency was set as a constant value or switched between two or more different frequencies. Impedance values were measured based on the current response and the applied potential profile. The measured impedance data were fitted for extracting each parameter of a circuit.

Figure 4:
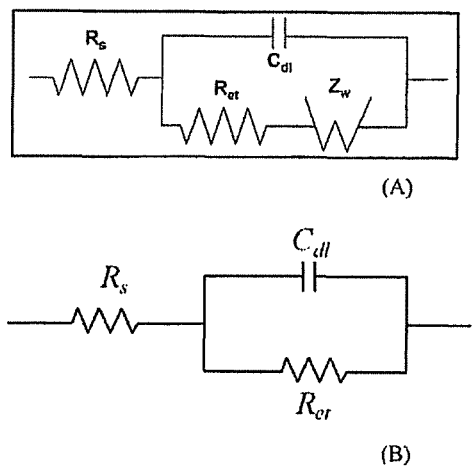
FIG. 4 shows (A) an equivalent circuit for fitting and obtaining $R_s$, $C_s$, $R_{et}$ and $Z_w$; and (B) a simplified circuit of (A)

FIG. 4(A) illustrates an equivalent circuit which consists of parameters of a solution resistance ($R_s$), a double-layer capacitance ($C_{dl}$), an electron-transfer resistance, $R_{et}$, and a Warburg impedance, $Z_w$. The $R_s$ arises from the finite conductance of the ions in bulk solution, and thus is generally not affect by the surface modification of the electrode. Since some materials, such as linkers and bio-molecules, for surface modification are dielectric substances, the $C_{dl}$ will change according to which kind of the material on the electrode surface. The $R_{et}$ relates to the kinetics of electron-transfer, and the $Z_w$ is a kind of resistance related to the mass transfer. By fitting the impedance data, measured at two or more (e.g., three) different frequencies, with the equivalent circuit, the parameters $R_s$, $C_{dl}$, $R_{et}$, and $Z_w$ are obtained.

To reduce the time of applying the potential at the different frequencies, the equivalent circuit shown in FIG. 4(A) is simplified into a circuit of FIG. 4(B) by selecting an appropriate frequency. After the simplification, the impedance of the circuit is:

$$Z = R_s + \frac{R_{et}}{1 + R_{et} j\omega C_{dl}}$$

where j is the imaginary unit and ω is angular frequency.

With a value $R_{et}j\omega C_{dl} \ll 1$ due to the selection of an appropriate frequency, $Z \cong R_s + R_{et}$, and $\Delta|Z| \cong \Delta R_{et}$. In other words, an approximate variation of the impedance ($\Delta R_{et}$) can be obtained with the potential scan at single frequency, with no need of fitting the equivalent circuit to extract the parameters, and thereby simplifying the back-end circuit design.

Preparation of Solutions in Electrochemical Experiments

In the following experiment, a phosphate buffered saline (PBS) solution supplied by UR (UR-PBS001) was used for the preparation of the capture probe and target analyte solutions. The electrolyte for the electrochemical experiment was a 1×PBS, pH 7.2 with 1 mM $K_3Fe(CN)_6/K_4Fe(CN)_6$ (Sigma-Aldrich) mixing solution and was prepared immediately before usage. The activation reagents, N-Hydroxysuccinimide (NHS) and N-Ethyl-N'-(3-dimethylaminopropyl) carbodiimide hydrochloride (EDC) for activation were obtained from Fluka (56480) and Sigma-Aldrich (E1769), respectively. The blocking reagent (for blocking unbinding site of a linker), Ethanolamine hydrochloride (ETA-HCl) was obtained from Sigma-Aldrich (E6133), and the regeneration reagent, glycine, for regenerating a surface of the capture probe bound electrode of the biochip were from and Sigma (50046). All the solutions were prepared with D.I. water purified through a Milli-Q system (Millipore).

The Biochip Structure

In the following experiment, the biochip comprises three electrodes: a 2-mm diameter Au as the working electrode; an Ag/AgCl electrode and Pt wire as the reference and counter electrode respectively. The 2-mm diameter Au working electrode was polished with a 0.05 μm alumina slurry and a microcloth pad and then ultrasonically cleaned in D.I. water.

Comparative Embodiment

The 12-Mercaptododecanoic acid ($HS(CH_2)_{11}COOH$, 12-MCA) obtained from Aldrich without further purification was used as an comparative example. The 12-MCA solution was prepared by dissolving in 95% ethanol.

In the comparative biochip, the 2-mm diameter Au electrode was immersed in the 12-MCA solution for 6 hours at room temperature. Afterwards, the 12-MCA modified electrode was rinsed with ethanol and D.I. water. Next, for the 12-MCA modified electrode, the COOH functional group in the 12-MCA was first activated by 400 mM EDC/100 mM NHS (1:1) for 40 minutes before immobilization of antiS100 (abcam) for another 40 minutes.

Figure 5:
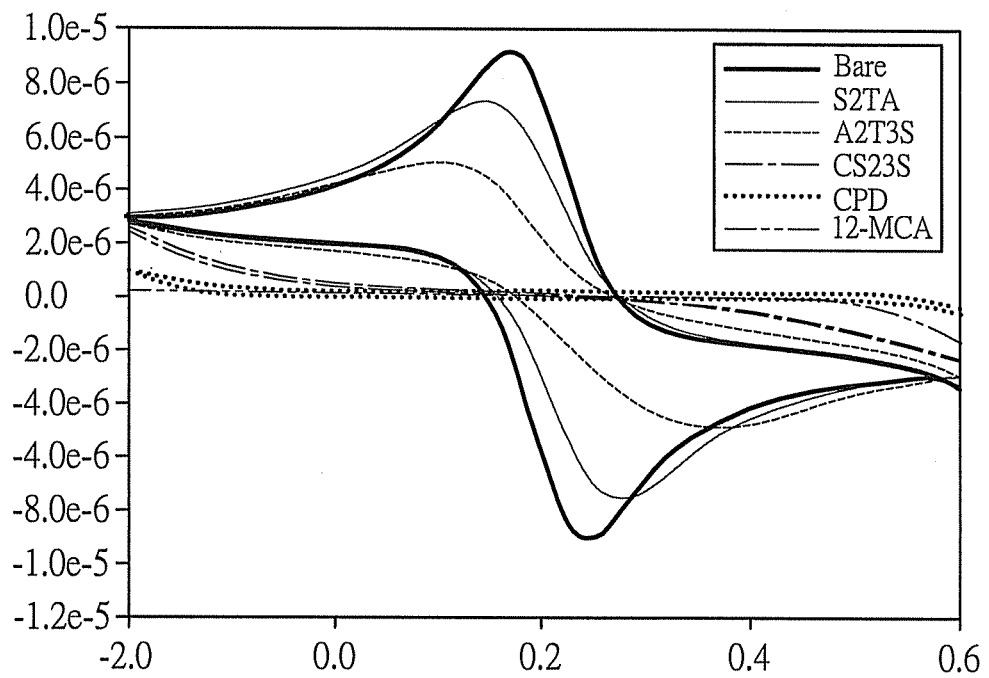
FIG. 5 is a diagram showing CV measurement of bare, S2TA, A2T3S, CS23S, CPD and 12-MCA modified electrodes.

Cyclic voltammetry is used to measure the blocking effect of a SAM modified on an electrode through the redox behavior of a reversible $Fe(CN)_6^{3-}/Fe(CN)_6^{4-}$ pair. In FIG. 5, oxidation and reduction (redox) peaks occurred at about 0.24 V and 0.17 V for the bare electrode. After modification of the 12-MCA, FIG. 5 shows that the peaks disappeared because of the blocking effect of the 12-MCA on the electron transfer of the $Fe(CN)_6^{3-}/Fe(CN)_6^{4-}$ pair. This indicated that the conventionally used long chain thiol linker was not suitable for use in a faradaic biochip.

Embodiment

Electrochemical Characterization

The molecules used as the linker or in the linker are shown in Table 1.

TABLE 1

| Short name | Molecular weight | Structure |
|---|---|---|
| S2TA | 240 | OHC—[thiophene]—[thiophene]—CH$_2$SH |
| A2T3S | 268 | OHC—[thiophene]—[thiophene]—(CH$_2$)$_3$—SH |
| CS23S | 284 | HO$_2$C—[thiophene]—[thiophene]—(CH$_2$)$_3$SH |
| CPD | 336 | HO$_2$C—[thiophene]—[thiophene]—(CH$_2$)$_6$SH |

The electrolyte for the electrochemical characterization was a 1×PBS, pH 7.2 with 1 mM $K_3Fe(CN)_6/K_4Fe(CN)_6$ (Sigma-Aldrich) mixing solution and was prepared immediately before usage. The molecules as the linker or part of the linker, 5'-(mercapto)-[2,2'-bithiophene]-5-carbaldehyde (and
5'-(mercapto)-[2,2'-bithiophene]-5-carboxylic acid),
5'-(mercaptomethyl)-[2,2'-bithiophene]-5-carbaldehyde (S2TA) (and
5'-(mercaptomethyl)-[2,2'-bithiophene]-5-carboxylic acid),
5'-(3-mercaptopropyl)-[2,2'-bithiophene]-5-carbaldehyde (A2T3S) (and
5'-(2-mercaptoethyl)-[2,2'-bithiophene]-5-carbaldehyde),
5'-(3-mercaptopropyl)-[2,2'-bithiophene]-5-carboxylic acid (CS23S) (and
5'-(2-mercaptoethyl)-[2,2'-bithiophene]-5-carboxylic acid), and
5'-(6-mercaptohexyl)-[2,2'-bithiophene]-5-carboxylic acid (CPD) were synthesized.

The S2TA and A2T3S solutions were prepared by dissolving in $CH_2Cl_2$, and CS23S and CPD were dissolved in THF. The concentrations were all 5 mM.

In the biochip, the 2-mm diameter Au electrode was immersed in S2TA, A2T3S, CS23C and CPD solutions respectively for 6 hours at room temperature. Afterwards; the S2TA and A2T3S modified electrodes (i.e., a glass substrate of the biochip having the Au-coated surface connected with the S2TA or A2T3S) were rinsed with $CH_2Cl_2$, ethanol and D.I. water. The CS23S and CPD modified electrodes were both rinsed with THF, ethanol and D.I. water. Since the functional groups of S2TA and A2T3S were CHO, the antiS100 bound to the S2TA and A2T3S without further activation.

The cyclic voltammetry (CV) was also used to measure the blocking effect of a SAM modified on an electrode through the redox behavior of a reversible $Fe(CN)_6^{3-}/Fe(CN)_6^{4-}$ pair. FIG. 5 shows the CV measurement of bare, S2TA, A2T3S, CS23S, CPD and 12-MCA modified electrode of the Comparative Embodiment. After modification of the molecules, the current peak values decreased a little bit and the difference between anode and cathode peak voltage, $\Delta E_p$, increased; however, the redox peak was still seen for the S2TA, A2T3S. This is due to the structure of the S2TA and the like has de-localized π electrons (in the form of a sulfur-containing aromatic heterocyclic group, such as a thiophene or thiophene derivative which can enhance the electron transfer, and thus is the most conductive.

By fitting the impedance data with an equivalent (i.e., Randles) circuit and analyzing with the Zview software, the electron transfer resistance, $R_{et}$, was estimated to be 1.22 kΩ, 5.78 kΩ and 1.58 MΩ for the bare electrode, the S2TA modified electrode and the 12MCA modified electrode respectively. The results were summarized in Table 2.

TABLE 2

| $R_{et}$ | Bare | S2TA | A2T3S | CS23S | CPD | 12-MCA |
|---|---|---|---|---|---|---|
| Average | 1.22E+03 | 5.78E+03 | 2.39E+04 | 1.28E+06 | 2.60E+06 | 1.58E+06 |
| STD | 1.09E+02 | 6.26E+02 | 1.34E+04 | 4.54E+05 | 5.82E+05 | 4.56E+05 |

The results demonstrated that the electron transfer resistance for the S2TA modified electrode was much lower, at about three orders, than for the case with the 12MCA modified electrode.

Figure 6:
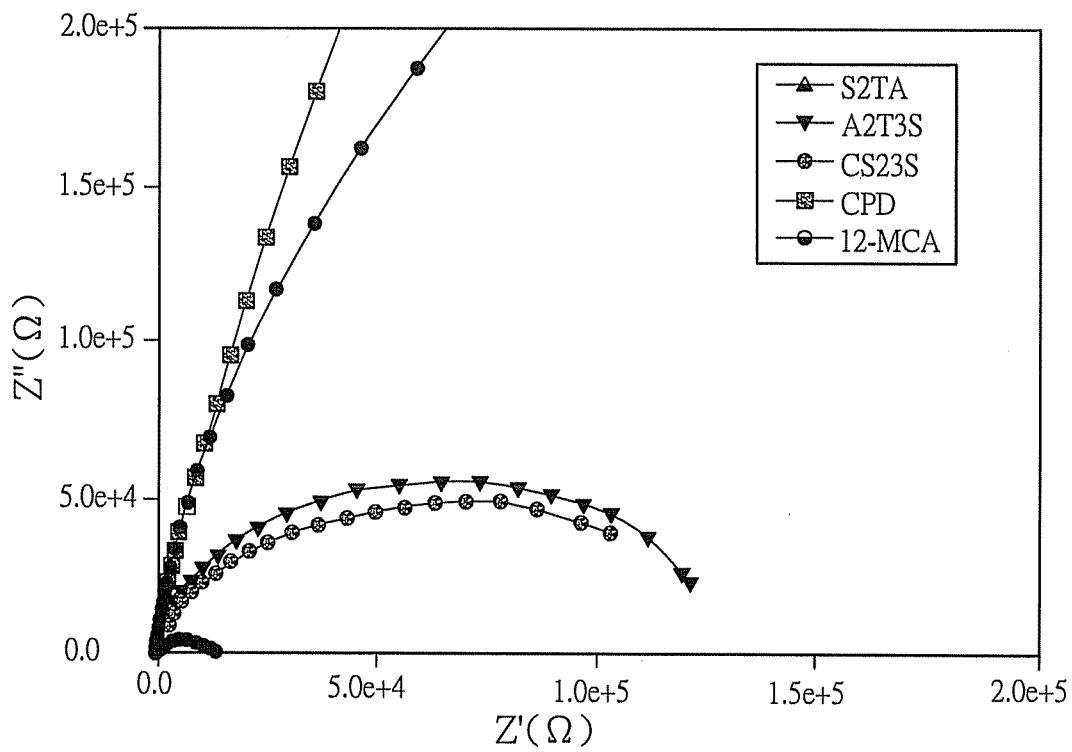
FIG. 6 is the impedance data of the biochip with the antigen recognition elements after the connection of a linker comprising S2TA.

Electrochemical Characteristic after Capture Probe (e.g., Antibody) Immobilization Since the electrostatic force plays an important role in the impedance measurement, it is better to compare the $R_{et}$ after the immobilization of the capture probe onto each molecule as the linker or a portion in the linker, to determine which linker is the best for faradaic impedance biochip. FIG. 6 shows the impedance data after antiS100 immobilization scanned from a range from 1 Hz to 100 kHz. By fitting the measured impedance data with the Randles circuit, the electron transfer resistance, $R_{et}$, for each molecule was estimated and summarized in Table 3, which shows the $R_{et}$ of various molecules respectively connected with the capture probe (antiS100). It is noted that 12MCA is an alkanethiol which is non-conductive.

TABLE 3

| $R_{et}$ | S2TA | A2T3S | CS23S | CPD | 12-MCA |
|---|---|---|---|---|---|
| Average | 1.173E+04 | 1.237E+05 | 1.071E+05 | 2.888E+06 | 1.235E+06 |
| STD | 1.440E+03 | 1.800E+04 | 2.541E+03 | 1.344E+06 | 2.758E+05 |

From the results, it is clear that the magnitude of $R_{et}$ is in the order of S2TA<A2T3S≅CS23S<CPD≅12-MCA. The impedance of S2TA after. antiS100 immobilization was about one order lower than that of A2T3S. This is due to the difference of methylene ($CH_2$) number and is agree to the results shown in Table 2. For A2T3S and CS23S, there is no large difference in $R_{et}$, which is inconsistent with the results in Table 2. The inconsistency may result from the fact that once the antiS100 immobilizes onto the SAM, the original electrostaic force between the SAM and redox pair disappears. Accordingly, the $R_{et}$ depends on the number of $CH_2$ only. The experimental results showed a tendency that the shorter the carbon chain ($CH_2$) is, the better the conductivity is. The S2TA had the highest conductivity because it has only one $CH_2$. It is noted that the conductivity was getting even better in case of ($CH_2$) being absent. Under this circumstance, the linker mainly relied on the two thiophenes therein to perform conductivity. The results showed that the carbon chain length should be as short as possible to reveal the advantage of thiophene and the like.

As a result, a linker comprising a molecule with a structure similar with the S2TA is much more suitable for a faradaic impedance biochip than the typically used conventional long chain thiol linker, since such structure offers a lower impedance baseline and has the potential for a better detection limit. The lower resistance also means having a higher current which is more beneficial for point-of-care applications since the electronic circuit system can be designed to be compact in size and low in cost.

Impedance Measurement of Antibody-Antigen (AntiS100-S100) Interaction

Normally, the common capture probe includes protein (e.g., antibody), DNA, enzyme and the like; the common target analyte (as a common biomarker) includes protein, DNA, cell, glucose, cardiomyopathic biomarkers (e.g., S100 and C-Reactive protein (CRP), Troponin I, CKMB and the like), cancer biomarkers (e.g., cancer antigen 125 (CA125), carcinoembryonic antigen (CEA), prostate-specific antigen (PSA) and the like), bacterium biomarkers (e.g., *E. Coli, staphylococcus* and the like), and virus (e.g., H1N1 and the like). The S100 and antiS100 were selected to conduct the impedance measurements.

For an antibody-antigen interaction measurement, the 1M ETA-HCl at pH 8.2 was introduced for 20 minutes after immobilization of antiS100 to block the unbinding site to prevent non-specific binding. Different concentrations of S100 (Sigma) which were prepared in 1×PBS (at pH 7.2), from 10 ng/mL to 10 μg/mL were then added to interact with the antiS100 for 15 minutes. To regenerate the surface, a 0.1M glycine, pH 2.5 was used.

Figure 7:
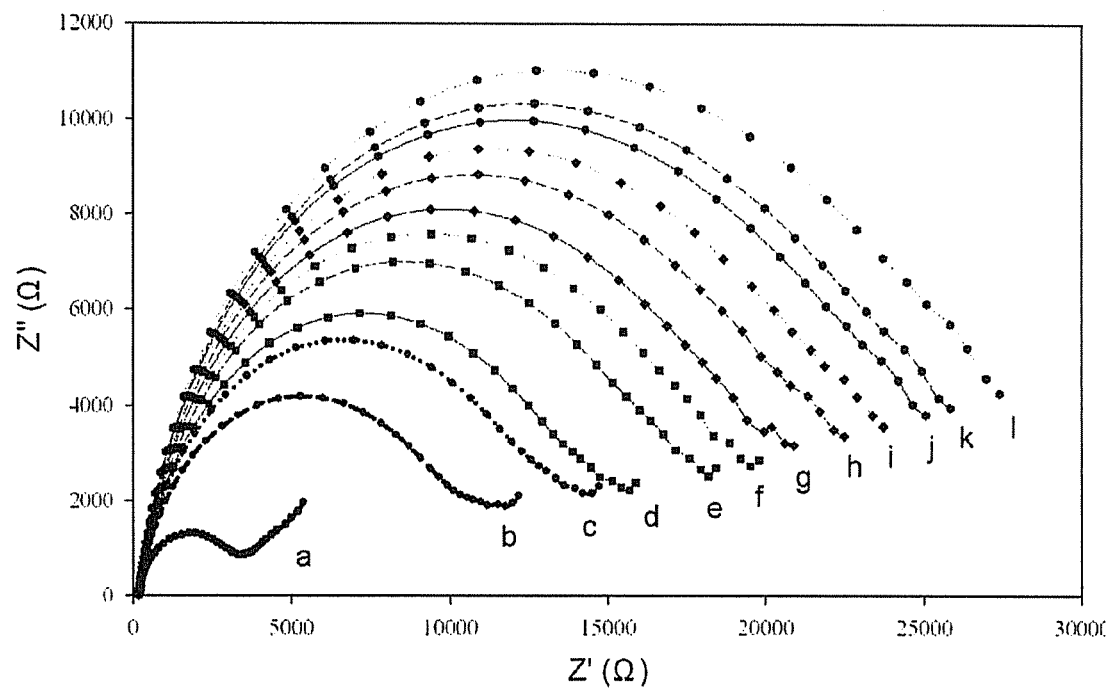
FIG. 7 is a diagram which shows impedance data of the biochip with the antigen recognition elements binding with a linker (e.g., S2TA modified electrode) in a 1×PBS solution with 1 mM Fe(CN)$_6^{3-/4-}$ after the addition of the antigen fluid samples.

S2TA was adopted to perform antiS100-S100 interactions measurement via EIS. FIG. 7 is a diagram which shows impedance data of the biochip with the antigen recognition elements binding with a linker (e.g., S2TA modified electrode) in a 1×PBS solution with 1 mM $Fe(CN)_6^{3-/4-}$ after the addition of the fluid samples, i.e., antiS100, ETA, and S100 antigen at different concentrations: (a) S2TA; (b) antiS100; (c) ETA; (d) 10 ng/ml S100, (e) 50 ng/ml S100, (f) 100 ng/ml S100, (g) 200 ng/ml S100, (h) 500 ng/ml S100, (i) 1 μg/ml S100, (j) 2 μg/ml S100, (k) 5 μg/ml S100, and (l) 10 μg/ml S100. From the figure, it is shown that the diameter of the semicircle increases after the addition of antiS100, ETA and S100 proteins. The increased diameter represents the increase of $R_{et}$. Since the antiS100 and ETA are nonconductive, the immobilization of antiS100 and binding of ETA formed steric hindrances which blocked the electron transfer of $Fe(CN)_6^{3-/4-}$. As the S100 protein, which is also nonconductive, interacted with the antiS100, a further increase in the $R_{et}$ was seen. As expected, when the concentration of the S100 protein was increased, the interaction between the antiS100 and S100 also increased. This resulted in a larger steric hindrance and an electrostatic repulsion force which then caused the impedance to change more dramatically.

The detailed values of $R_s$, $R_{et}$ and $C_{dl}$ can be extracted by fitting the data into the equivalent circuit model, and the results listed in Table 4.

TABLE 4

|  | $R_s$ (Ω) | $R_{et}$ (Ω) | $C_{dl}$ (F) |
|---|---|---|---|
| S2TA | 140.7 | 3043 | 7.20E-07 |
| AntiS100 (200 μg/ml) | 145.5 | 9972 | 6.55E-07 |
| ETA | 147.7 | 12609 | 6.65E-07 |
| S100 (0.01 μg/ml) | 149.6 | 13846 | 6.53E-07 |
| S100 (0.05 μg/ml) | 151.1 | 16435 | 6.83E-07 |
| S100 (0.1 μg/ml) | 152.5 | 17812 | 6.91E-07 |
| S100 (0.2 μg/ml) | 153.8 | 18971 | 6.94E-07 |
| S100 (0.5 μg/ml) | 154.7 | 20623 | 6.91E-07 |
| S100 (1 μg/ml) | 154.6 | 21892 | 6.93E-07 |
| S100 (2 μg/ml) | 154 | 23266 | 6.91E-07 |
| S100 (5 μg/ml) | 155 | 24026 | 6.90E-07 |
| S100 (10 μg/ml) | 155.2 | 25624 | 6.92E-07 |

From the table, it is found that the changes in $R_s$ and $C_{dl}$ are small compare to that in $R_{et}$. The data are consistent with the prediction since $R_s$ is only related to the composition of electrolyte. The $C_{dl}$ will not change a lot as the existing of redox current. Generally, the $R_{et}$ is the parameter changed the most in a faradaic impedance biochip. To quantify the S100, a parameter is defined as:

$$\Delta R_{et} = R_{et(S100)} - R_{et(ETA)},$$

where $R_{et(S100)}$ is the $R_{et}$ value measured after adding the S100 protein at different concentrations, and $R_{et(ETA)}$ represents the $R_{et}$ value before adding the S100 protein. Table 5 shows the detail $R_{et}$ change of each concentration of S100.

TABLE 5

| S100 concentration (µg/ml) | $\Delta R_{et, mean}$ (Ω) | STD (Ω) | RSD (%) | $\Delta R_{et, mean}/R_{et, antiS100}$ (%) |
|---|---|---|---|---|
| 0.0100 | 1322.25 | 151.37 | 11.45 | 11.93 |
| 0.0500 | 3989.00 | 647.08 | 16.22 | 35.98 |
| 0.1000 | 5432.25 | 828.86 | 15.26 | 49.00 |
| 0.2000 | 6632.75 | 989.93 | 14.92 | 59.83 |
| 0.5000 | 8396.25 | 648.66 | 7.73 | 75.73 |
| 1.0000 | 9559.75 | 912.75 | 9.55 | 86.23 |
| 2.0000 | 10773.25 | 919.25 | 8.53 | 97.17 |
| 5.0000 | 11794.75 | 1197.73 | 10.15 | 106.39 |
| 10.0000 | 13342.00 | 1551.74 | 11.63 | 120.34 |

Figure 8:
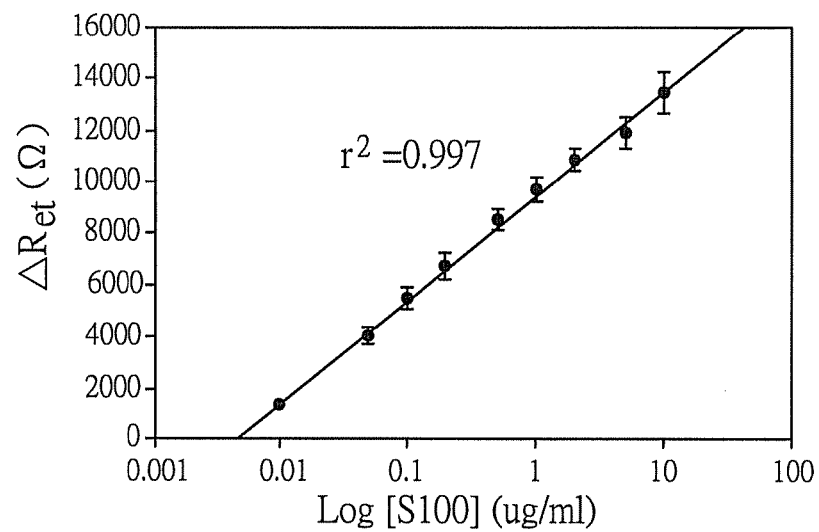
FIG. 8 shows a plot for the calculated $R_{et}$ change as a function of S100 concentration from 10 ng/ml to 10 µg/ml (n=4).

FIG. 8 shows a linear relationship between $\Delta R_{et}$ and the S100 protein which was found to be in the range between 10 ng/ml to 10 µg/ml and where the detection limit was about 10 ng/ml (0.5 nM). The calculated relative standard deviation (RSD, n=4) was about 10 to 15%. Compared to the prior art using a long chain thiol as a linker, the detection limit in our system is much improved (82 nM vs. 0.5 nM) as the conductive linker can increase the S/N and further lower the detection limit.

Based on the above electrochemical characterization, the tested molecules as the linker or a portion in the linker are as follows,

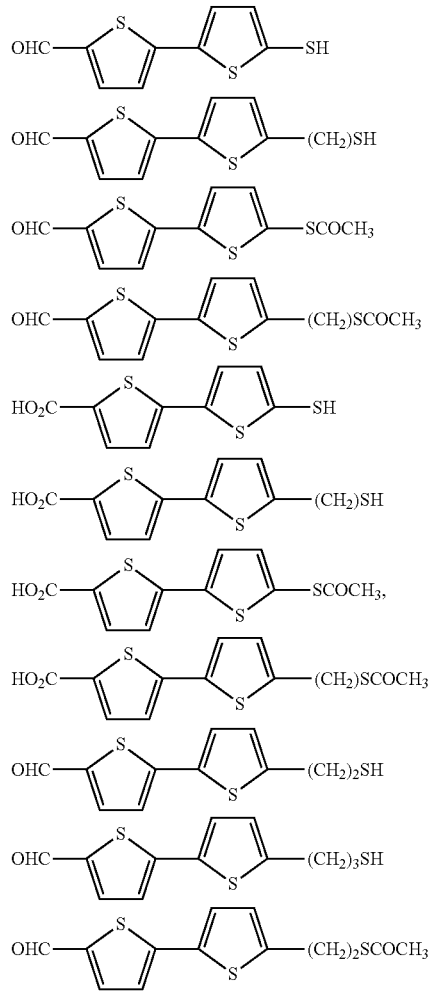

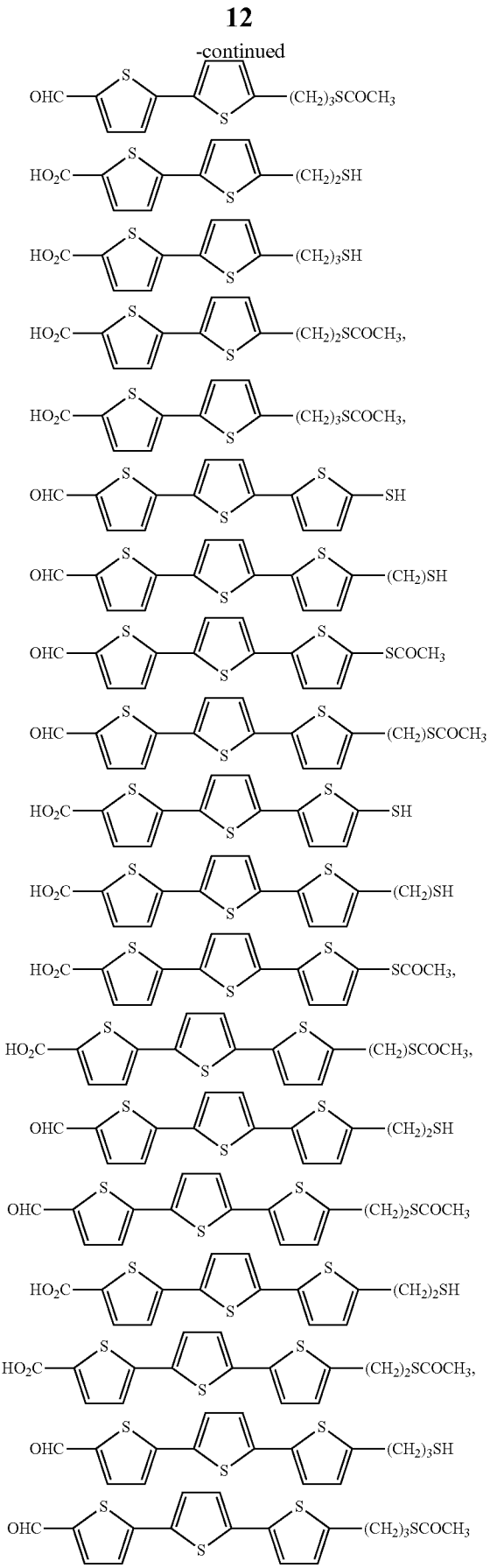

-continued

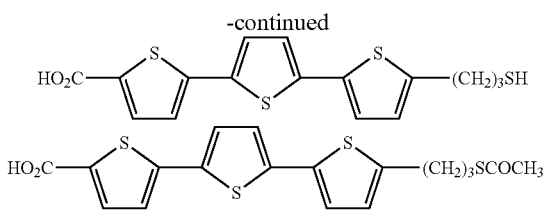

The results of the measured impedance data $R_{et}$ for the above molecules exhibited that $R_{et}$ depended only on the number (or length) of (CH$_2$), as well as comply with the prediction that the shorter the carbon chain (CH$_2$) is, the better the conductivity is.

Given the above, the linker and the biochip comprising the linker according to the embodiments of the present invention has the advantages of low cost, compact size, and convenient calibration. The advantage of increasing faradaic current is that the electronic circuit for an impedance biochip can be designed more compact and at low cost, and thus is suitable for point-of-care applications.

The present invention has been described using exemplary preferred embodiments. However, it is to be understood that the scope of the disclosure is not limited to the disclosed arrangements. The scope of the claims, therefore, should be accorded the broadest interpretation, so as to encompass all such modifications and similar arrangements.

What is claimed is:

1. A linker for joining an electrode and a capture probe on a biochip, comprising a compound of formula (I):

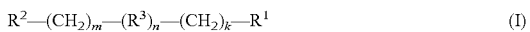

wherein
  $R^1$ is a functional group for binding the capture probe which is protein, DNA, RNA, or enzyme, wherein the $R^1$ functional group is
    —C(=O)—OH,
    —C(=O)H,
    —NH2, or
    epoxide;
  $R^2$ is a functional group for connecting the electrode selected from the group consisting of Au, Pt, Ag, and ITO, wherein the $R^2$ functional group is
    —SH,
    —S—C(=O)CH$_3$,
    sulfide,
    disulfide, or
    silane;
  $R^3$ is a thiophene or thiophene derivative;
  n is an integer of from 1 to 4;
  m is an integer of from 0 to 5;
  k is an integer of from 0 to 5.

2. The linker of claim 1, wherein the compound is selected from the group consisting of:
  5'-(mercapto)-[2,2'-bithiophene]-5-carbaldehyde,
  5'-(mercapto)-[2,2'-bithiophene]-5-carboxylic acid,
  5'-(mercaptomethyl)-[2,2'-bithiophene]-5-carbaldehyde,
  5'-(mercaptomethyl)-[2,2'-bithiophene]-5-carboxylic acid,
  5'-(2-mercaptoethyl)-[2,2'-bithiophene]-5-carbaldehyde,
  5'-(2-mercaptoethyl)-[2,2'-bithiophene]-5-carboxylic acid,
  5'-(3-mercaptopropyl)-[2,2'-bithiophene]-5-carbaldehyde, and
  5'-(3-mercaptopropyl)-[2,2'-bithiophene]-5-carboxylic acid.

3. A biochip for quantitatively detecting a concentration of a target analyte in a fluid sample, comprising:
  at least two electrodes;
  the linker of claim 1; and
  a capture probe for interacting with the target analyte in the fluid sample, wherein the linker has two terminals individually connecting the capture probe and at least one of the electrodes.

4. The biochip of claim 3, wherein the electrode is a material made of selected from the group consisting of Au, Pt, Ag, and ITO.

5. The biochip of claim 3, wherein the capture probe is at least one selected from the group consisting of protein, DNA, RNA, and enzyme.

6. A method of quantitatively detecting a concentration of a target analyte in a fluid sample, comprising steps of:
  providing the fluid sample on the biochip of claim 3;
  providing a redox species into the fluid sample;
  applying a potential profile with an alternative current (AC) frequency to the two electrodes in the biochip during a period of time and measuring a current response needed to maintain the potential profile simultaneously; and
  associating the current response to the concentration of the target analyte in the fluid sample.

7. The method of claim 6, wherein the AC in the potential profile is a sine wave, a triangle wave, a square wave or a combination of a sine wave, a triangle wave and/or a square wave.

8. The method of claim 6, wherein the potential profile further comprises a direct current (DC) bias.

9. The method of claim 8, wherein the DC bias keeps constant during the period of time.

10. The method of claim 8, wherein the DC bias varies during the period of time.

11. The method of claim 8, wherein the DC bias ranges from −0.5 to 0.5 V.

12. The method of claim 7, wherein the AC has an amplitude ranging from 0.001 to 0.05 V.

13. The method of claim 6, wherein the target analyte is selected from the group consisting of protein, DNA, cell, glucose, cardiomyopathic biomarkers, cancer biomarkers, carcinoembryonic antigen (CEA), prostate-specific antigen (PSA), bacterium biomarkers, and virus.

14. The method of claim 6, wherein the potential profile switches more than one AC frequency during the period of time.

15. The method of claim 6, wherein the redox specie is $Fe(CN)_6^{3-/4-}$ or $Ru(NH_3)_6^{2+/3+}$.

* * * * *